(12) United States Patent
Bonner et al.

(10) Patent No.: US 9,737,473 B2
(45) Date of Patent: *Aug. 22, 2017

(54) LEAVE-ON COMPOSITIONS CONTAINING CELLULOSE MATERIALS

(71) Applicant: JOHNSON & JOHNSON CONSUMER INC., Skillman, NJ (US)

(72) Inventors: Patricia Bonner, Branchburg, NJ (US); Claudia Kaminski, Milford, NJ (US); Danielle Lima Lorenzetti, Jacarei/SP (BR); Prithwiraj Maitra, Hillsborough, NJ (US); Juliana Salles Moscardi, Sao Jose dos Campos/SP (BR); Jeffrey M. Wu, Princeton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/178,593

(22) Filed: Jun. 10, 2016

(65) Prior Publication Data

US 2016/0279047 A1    Sep. 29, 2016

Related U.S. Application Data

(63) Continuation of application No. 14/259,463, filed on Apr. 23, 2014, now Pat. No. 9,364,416, which is a
(Continued)

(51) Int. Cl.
*A61K 8/73* (2006.01)
*A61K 8/02* (2006.01)
(Continued)

(52) U.S. Cl.
CPC ............ *A61K 8/731* (2013.01); *A61K 8/0241* (2013.01); *A61K 8/0245* (2013.01); *A61K 8/11* (2013.01);
(Continued)

(58) Field of Classification Search
None
See application file for complete search history.

(56) References Cited

U.S. PATENT DOCUMENTS

| 1,873,030 A | 8/1932 | Quinn |
| 2,129,264 A | 9/1938 | Baxter et al. |

(Continued)

FOREIGN PATENT DOCUMENTS

| EP | 819797 A | 1/1998 |
| EP | 829259 A | 3/1998 |

(Continued)

OTHER PUBLICATIONS

JP1990-174709 (Yoshihito) English Translation. pp. 1-19. (2016).*
(Continued)

*Primary Examiner* — Ernst V Arnold
*Assistant Examiner* — Kyung Sook Chang

(57) ABSTRACT

The compositions and methods of this invention relate to a leave-on skin care composition containing hydrophobic, linear cellulose particles having an average length of from about 1 to about 500 μm, a particle aspect ratio from about 2 to about 25 and an average thickness of from about 1 to about 500 μm; and a cosmetically acceptable carrier.

12 Claims, 7 Drawing Sheets

Related U.S. Application Data continuation of application No. 13/799,293, filed on Mar. 13, 2013, now abandoned, which is a continuation-in-part of application No. 13/673,430, filed on Nov. 9, 2012, now abandoned.

(51) Int. Cl.
  *A61K 8/11* (2006.01)
  *A61Q 19/00* (2006.01)

(52) U.S. Cl.
  CPC ...... *A61Q 19/008* (2013.01); *A61K 2800/412* (2013.01)

(56) References Cited

U.S. PATENT DOCUMENTS

| | | | |
|---|---|---|---|
| 2,178,353 A | 10/1939 | Werntz | |
| 2,774,786 A | 12/1956 | Erickson | |
| 2,813,898 A | 11/1957 | Gaertner | |
| 2,828,332 A | 3/1958 | Gaertner | |
| 3,278,383 A | 10/1966 | White et al. | |
| 3,318,817 A | 5/1967 | Smith, Jr. | |
| 3,755,560 A | 8/1973 | Dickerty et al. | |
| 4,215,064 A | 7/1980 | Lindemann et al. | |
| 4,233,192 A | 11/1980 | Lindemann et al. | |
| 4,254,105 A | 3/1981 | Fukuda | |
| 4,272,514 A | 6/1981 | Spence | |
| 4,372,869 A | 2/1983 | Lindemann et al. | |
| 4,380,637 A | 4/1983 | Lindemann et al. | |
| 4,382,036 A | 5/1983 | Lindemann et al. | |
| 4,421,769 A | 12/1983 | Dixon et al. | |
| 4,490,764 A | 12/1984 | Butz | |
| 4,559,243 A | 12/1985 | Passler et al. | |
| 4,606,958 A | 8/1986 | Haq et al. | |
| 4,617,414 A | 10/1986 | Lukenbach et al. | |
| 4,960,764 A | 10/1990 | Figueroa, Jr. et al. | |
| 5,415,804 A | 5/1995 | Minami et al. | |
| 5,654,362 A | 8/1997 | Schulz, Jr. et al. | |
| 5,763,497 A | 6/1998 | Ikeda et al. | |
| 5,830,485 A | 11/1998 | Gueret et al. | |
| 5,891,424 A | 4/1999 | Bretzler et al. | |
| 5,919,437 A | 7/1999 | Lee et al. | |
| 5,964,983 A | 10/1999 | Dinand et al. | |
| 5,965,146 A | 10/1999 | Franzke et al. | |
| 5,976,514 A | 11/1999 | Guskey et al. | |
| 6,001,338 A | 12/1999 | Mondet | |
| 6,060,546 A | 5/2000 | Powell et al. | |
| 6,123,951 A | 9/2000 | Gueret et al. | |
| 6,294,509 B1 | 9/2001 | Meiwa et al. | |
| 6,342,237 B1 | 1/2002 | Bara | |
| 6,491,931 B1 | 12/2002 | Collin | |
| 6,503,520 B1 | 1/2003 | Afriat | |
| 6,534,071 B1 | 3/2003 | Tournilhac et al. | |
| 6,607,734 B1 | 8/2003 | Afriat | |
| 6,620,419 B1 | 9/2003 | Lintner | |
| 6,656,487 B2 | 12/2003 | Afriat et al. | |
| 6,689,345 B2 | 2/2004 | Jager Lezer | |
| 6,906,106 B2 | 6/2005 | Chevalier | |
| 7,094,317 B2 | 8/2006 | Lundberg et al. | |
| 7,378,103 B2 | 5/2008 | Kanji et al. | |
| 7,594,619 B2 | 9/2009 | Ghere, Jr. et al. | |
| 7,780,971 B2 | 8/2010 | Chevalier et al. | |
| 7,803,403 B2 | 9/2010 | Librizzi et al. | |
| 7,820,151 B2 | 10/2010 | de la Poterie et al. | |
| 7,846,461 B2 | 12/2010 | Hwang et al. | |
| 8,029,773 B2 | 10/2011 | Loginova et al. | |
| 8,105,691 B2 | 1/2012 | Takeuchi et al. | |
| 8,772,359 B2 | 7/2014 | Swazey | |
| 8,894,980 B2 | 11/2014 | Kawasaki et al. | |
| 8,894,981 B2 | 11/2014 | Shimizu et al. | |
| 9,018,189 B2 | 4/2015 | Herranen et al. | |
| 9,045,716 B2 | 6/2015 | Swazey et al. | |
| 9,089,502 B2 | 7/2015 | Bui et al. | |
| 2002/0028222 A1 | 3/2002 | Afriat | |
| 2002/0031533 A1 | 3/2002 | Afriat | |
| 2002/0182238 A1 | 12/2002 | Creton | |
| 2002/0192251 A1 | 12/2002 | Collin | |
| 2002/0197289 A1 | 12/2002 | Chevalier et al. | |
| 2003/0024556 A1 | 2/2003 | Guiramand et al. | |
| 2003/0086951 A9 | 5/2003 | Piot et al. | |
| 2003/0086962 A1 | 5/2003 | Westerfield et al. | |
| 2004/0142008 A1 | 7/2004 | Chevalier et al. | |
| 2004/0161435 A1 | 8/2004 | Gupta | |
| 2005/0002996 A1 | 1/2005 | Sojka | |
| 2005/0175650 A1 | 8/2005 | Hadasch et al. | |
| 2005/0191259 A1 | 9/2005 | Feng | |
| 2006/0008485 A1 | 1/2006 | Ferone et al. | |
| 2006/0029625 A1 | 2/2006 | Niebauer | |
| 2006/0182699 A1 | 8/2006 | Taylor et al. | |
| 2006/0246027 A1 | 11/2006 | Tanner | |
| 2006/0257348 A1 | 11/2006 | Walters et al. | |
| 2006/0275232 A1 | 12/2006 | Chevalier | |
| 2007/0111910 A1 | 5/2007 | Walters et al. | |
| 2007/0141095 A1 | 6/2007 | Simonnet | |
| 2008/0138368 A1 | 6/2008 | Lezer | |
| 2008/0241087 A1 | 10/2008 | Farsedakis et al. | |
| 2009/0263342 A1 | 10/2009 | Glenn, Jr. et al. | |
| 2009/0269299 A1 | 10/2009 | Cassin | |
| 2009/0269376 A1 | 10/2009 | Lundberg et al. | |
| 2009/0291057 A1* | 11/2009 | Chang .................. | A61K 8/463 424/70.21 |
| 2010/0009891 A1 | 1/2010 | Canto et al. | |
| 2010/0221294 A1 | 9/2010 | Kurek et al. | |
| 2010/0286583 A1 | 11/2010 | Torres | |
| 2011/0081388 A1 | 4/2011 | Oh et al. | |
| 2011/0223223 A1 | 9/2011 | Murata et al. | |
| 2011/0250250 A1 | 10/2011 | Kishida et al. | |
| 2011/0319306 A1 | 12/2011 | Walters et al. | |
| 2011/0319307 A1 | 12/2011 | Gunn et al. | |
| 2012/0142909 A1 | 6/2012 | Lundberg | |
| 2013/0340781 A1 | 12/2013 | Liebel et al. | |
| 2014/0134217 A1 | 5/2014 | Bonner et al. | |
| 2014/0134218 A1 | 5/2014 | Bonner et al. | |
| 2014/0134219 A1 | 5/2014 | Bonner et al. | |
| 2014/0227331 A1 | 8/2014 | Bonner et al. | |
| 2014/0234384 A1 | 8/2014 | Bonner et al. | |
| 2014/0286887 A1 | 9/2014 | Sandler et al. | |
| 2014/0357721 A1 | 12/2014 | Shirao et al. | |
| 2015/0037383 A1 | 2/2015 | Bonner et al. | |
| 2015/0040933 A1 | 2/2015 | Bonner et al. | |
| 2015/0110841 A1 | 4/2015 | Wiechers et al. | |
| 2015/0164779 A1 | 6/2015 | Botto et al. | |
| 2015/0297469 A1 | 10/2015 | Hayashi et al. | |

FOREIGN PATENT DOCUMENTS

| | | |
|---|---|---|
| EP | 1813252 A | 8/2007 |
| EP | 2332519 A1 | 6/2011 |
| EP | 2382961 A | 11/2011 |
| EP | 2907498 A | 8/2015 |
| JP | S63238008 A | 10/1988 |
| JP | 1990-174709 A | 7/1990 |
| JP | H11152206 A | 6/1999 |
| JP | 2007056236 A | 3/2007 |
| KR | 20090056295 A | 6/2009 |
| WO | WO 2008/129955 A | 10/2008 |
| WO | WO 2009/037347 A | 3/2009 |
| WO | WO 2011/105535 A | 9/2011 |
| WO | WO 2012/133018 A | 10/2012 |
| WO | WO 2013/039483 A | 3/2013 |
| WO | WO 2013/186715 A | 12/2013 |
| WO | WO 2013/186720 A | 12/2013 |
| WO | WO 2014/185284 A | 11/2014 |

OTHER PUBLICATIONS

U.S. Appl. No. 13/673,430, filed Nov. 9, 2012, Abandoned.
U.S. Appl. No. 13/673,477, filed Nov. 9, 2012, Abandoned.
U.S. Appl. No. 61/724,646, filed Nov. 9, 2012, Expired.
U.S. Appl. No. 13/799,467, filed Mar. 13, 2013, Abandoned.
Awapaper, "Regenerated Fibers" [retrieved from on-line website: http://www.awapaper.co.jp/e/products/detail/s_m01c.html, accessed Mar. 2, 2016].

(56) References Cited

OTHER PUBLICATIONS

*The International Cosmetic Ingredient Dictionary and Handbook*, 7th Edition (1997) ("ICI Handbook"), eds. Wenninger and McEwen, The Cosmetic, Toiletry and Fragrance Assoc., Washington, D.C., pp. 1612, 1613, 1626, 1650-1667, 1673-1686 and 1693-1697.
McCutcheon's Detergents and Emulsifiers, North American Edition (1986), pp. 317-324.
Sagarin, *Cosmetics, Science and Technology*, 2nd Edition (1972), vol. 1, pp. 32-43 and pp. 72-73.
Thielmann et al., "Determination of the surface energy distributions of different processed lactose", *Drug Development and Industrial Pharmacy*, 33(11):1240-53, Nov. 2007.
Yla-Maihaniemi et al., "Inverse gas chromatographic method for measuring the dispersive surface energy distribution for particulates", *Langmuir*, vol. 24(17):9551-7, Sep. 2, 2008.
Olson Eric "Particle shape factors and their use in image analysis part II: Practical Applications" Autumn 2011.
Fiberstar: "Imulsi-Fi", Imulsi-Fi A30 Information Booklet, Apr. 1, 2012, pp. 1-28 (XP007920784).
International search report mailed Feb. 26, 2014, for corresponding international application PCT/US2013/068687.

\* cited by examiner

IR Spectra of Cotton Powders and Cellulose

LEAVE-ON COMPOSITIONS CONTAINING CELLULOSE MATERIALS

This application is a continuation of U.S. application Ser. No. 14/259,463 filed Apr. 23, 2014, which is a continuation of U.S. application Ser. No. 13/799,293 filed Mar. 13, 2013, which is a continuation-in-part of U.S. application Ser. No. 13/673,430 filed Nov. 9, 2012, the complete disclosures of which are hereby incorporated herein by reference for all purposes.

FIELD OF THE INVENTION

The compositions of this invention relate to leave-on skin care compositions containing hydrophobic, linear cellulose particles that reduce the presence of oil-related substances on skin.

BACKGROUND OF THE INVENTION

Oily skin is shiny, thick and dull colored. Often, chronically oily skin has coarse pores and pimples and other embarrassing blemishes. Furthermore, chronically oily skin can be prone to developing blackheads. In this type of skin, the oil-producing sebaceous glands are overactive and produce more oil than is needed. The oil flows out of the follicles and gives the skin an undesirable greasy shine. The pores are enlarged and the skin has a coarse look. While oily skin is common in teenagers, it can occur at any age.

Generally, individuals having oily skin attempt to treat areas of oiliness in order to prevent outbreaks of acne and to diminish shininess. The conventional treatments available include soaps or surfactant based cleansers, astringents with alcohol and clay or mud masks. Oil absorbing materials such as clay or salt have also been used to attempt to treat this condition.

Individuals having oily or shiny skin conditions prefer a treatment that can remove the shine without drying the skin. However, there is a lack of effective skin care products on the market today that address this consumer need. Oil absorbing powders such as silica, aluminum starch and talc have been used in the cleansing products to help dry the skin surface oil, but they also tend to dry the skin and oily and shiny skin tend to come back quickly, usually in two to three hours.

Thus, it would be desirable to have compositions and methods of treatment that address the condition of oily skin while keeping skin hydrated.

SUMMARY OF THE INVENTION

The compositions and methods of this invention relate to a leave-on skin care composition comprising hydrophobic, linear cellulose particles having an average length of from about 1 to about 500 µm, a particle aspect ratio from about 2 to about 25 and an average thickness of from about 1 to about 500 µm; and a cosmetically acceptable carrier.

DETAILED DESCRIPTION OF THE PREFERRED EMBODIMENTS

Hydrophobic, Linear Cellulose Particles

Figure 1:
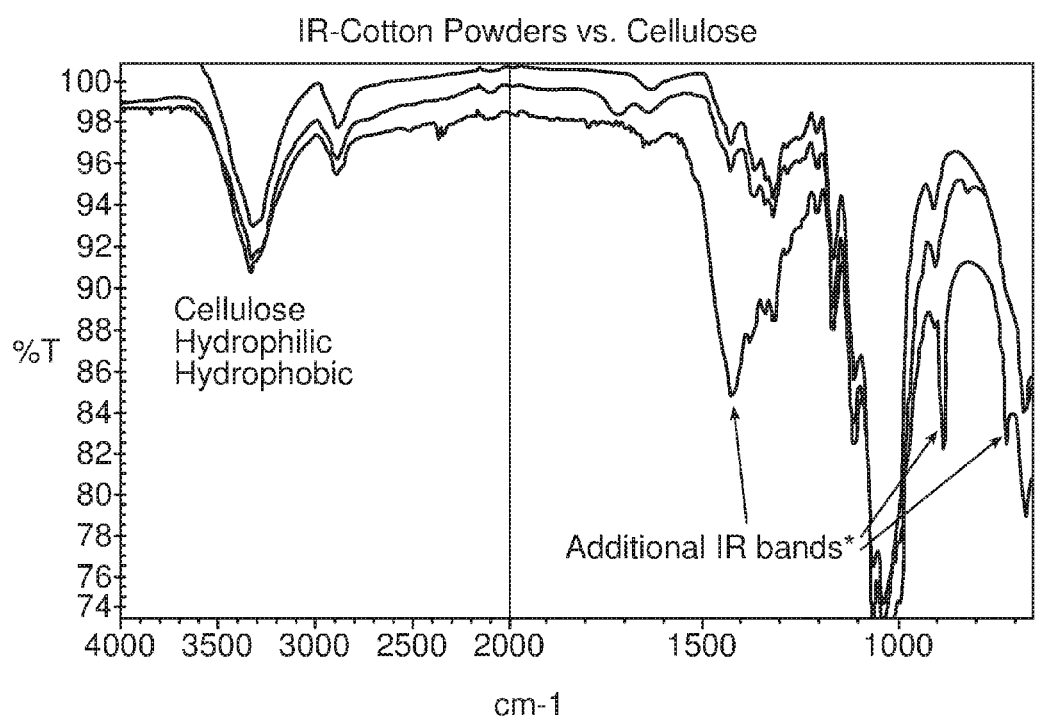
FIG. 1 is a graph of Infrared spectra of various cotton particles and cellulose.

As used herein, the term "hydrophobic" means materials having a surface contact angle with squalene of less than 40 degrees and/or a surface contact angle with water of greater than 90 degrees. The term "surface contact angle" means the internal angle between a surface and a liquid droplet resting on that surface. Surface tension (liquid) or surface free energy (solid) is considered to be a resulting balance between the molecular interactions of the liquid-liquid and air-liquid or solid-solid and air-solid phase at the interfacial layer. The term "contact angle" is a convenient and useful parameter to determine the surface free energy and wettability of any given solid surface due to the non-deformability of the solid. The contact angle is determined by measuring the angle formed between substrate surface where a liquid droplet is placed and the tangent to the drop surface from the contact point. High contact angles correspond to poor wetting of the surface by the liquid and low contact angles signify good wetting. If a liquid spreads on the surface, the contact angle is considered to be zero and complete wetting is said to occur.

Contact angle measurements can be employed to determine the wettability of human skin by a variety of liquids, including hydrophobic liquids such as squalene and hydrophilic liquids, including water. A smaller contact angle with a non-polar liquid (such as squalene) corresponds to a more hydrophobic material while a smaller water contact angle corresponds to a more hydrophilic material.

In accordance with the methods and compositions of this invention, the water contact angle of the hydrophobic, linear cellulose particles is preferably greater than 90 degrees, preferably greater than 100 degrees and more preferably greater than 120 degrees.

As used herein, the term "oil absorption capacity and retention" refers to the weight percentage of the oil absorbed by the hydrophobic, linear cellulose particles useful in the compositions and methods of this invention. High oil absorption capacity and retention corresponds to an increased hydrophobic property. The oil absorption capacity and retention of the hydrophobic, linear cellulose particles of the compositions of this invention is preferably from about 150 to about 500, and more preferably from about 300 to about 500 (% weight oil/weight particles).

As used herein, the term "particle" means a small localized object to which can be ascribed physical properties such as volume or mass. As used herein, "powder" is used synonymously to "particle", as defined herein.

As used herein, the term "linear particle" means a particle having one dimension ("length") that is greater than another dimension ("width"). Linear particles may be measured and defined by size by subjecting such particles to analysis with respect to a series of sieves having different mesh sizes. Generally, a sample of linear particles may have a distribution of particle sizes throughout the sample. Thus, linear particle sizes as expressed herein are expressed as an average particle size and reflect the average length of the particles contained within the sample.

Preferably, the size of linear particles useful in the compositions and methods of this invention is less than about 500 μm in length, more preferably, it ranges from about 2 to about 500 μm, and most preferably from about 10 to about 300 μm.

The preferred width of linear particles useful in the compositions and methods of this invention are about 1 to about 25 μm. More preferably, they are from about 1 to about 20 μm in width.

As used herein, the term "particle aspect ratio" means the ratio of the length of a particle to its width.

Preferably, the particle aspect ratio of the particles useful in the compositions and methods of this invention is from about 2 to about 20. More preferably, the particle aspect ratio is from about 2 to about 15 and most preferably, from about 2 to about 10.

As used herein, the term "cellulose" refers to a polysaccharide material consisting of long unbranched chains of linked glucose units, having the chemical structure set forth in Formula I below:

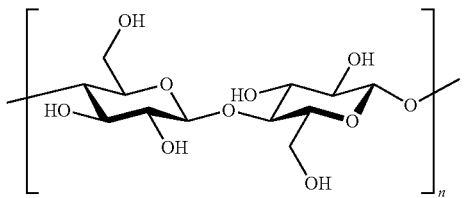

Cellulose, the most abundant biomass on the surface of the earth, has provided mankind with functional, low cost and renewable raw material.

Cellulose materials useful in the compositions and methods of this invention may be derived from cotton, corn, wood pulp and bamboo pulp, silk, cork and the like. Preferably, the cellulose materials useful in the compositions of this invention are derived from cotton. More preferably, the cellulosic particles are from fibers recovered from post-industrial scrap. Such scrap is derived from waste or other pre-consumer cotton products from, for example, the apparel, carpet, furniture and household goods industries. Synthetic or regenerated cotton or cellulose materials may also be used as sources for the cellulose particles useful in the compositions and methods of this invention, including rayon, viscose, cellophane, and other cellulosic materials with a uniform and reproducible molecular size and distribution.

The cellulose materials useful in the compositions and methods of this invention may be derived directly from the source plant (referred to herein as, "Raw" particles) or may be generated from cloth or nonwoven materials previously formed from plant or cellulose fibers (referred to herein as "regenerated" particles). For example, cotton cloth may be processed so as to break the cloth into small particles and/or uniform fiber length by cutting the length of the cotton fibers from inches to microns. This random-cut fiber is available in several grades, white, dark, and unbleached, with average fiber lengths from about 1 micron to about 500 microns and preferably from about 2 microns to about 300 microns.

Typical mechanical milling processes such as those useful in cutting down the size of the cellulose materials useful in the compositions and methods of this invention, for example, are described in U.S. Pat. No. 7,594,619 and U.S. Pat. No. 6,656,487, which are hereby incorporated herein by reference.

Generally, the cellulose particles useful in the compositions of this invention may be processed according to the following methods:

One such method comprises mixing a cellulosic material derived from scrap, as defined above, with at least one of grinding aids selected from the group including water, fatty acids, synthetic polymers and organic solvents, and, after mixing, mechanically grinding the mixture.

Another method of obtaining cellulose particles is freezing a cellulosic material derived from post-industrial scrap at a low temperature, and then mechanically grinding said frozen material. The cellulose particles useful in the compositions and methods of this invention may be further treated with hydrophobic agents to yield hydrophobic cellulose particles. For example, a hydrophobic coating agent may be used to treat the cellulose particles. The hydrophobic coating agent may be any such agent known to one of skill in the art. Preferred hydrophobic coating agents react chemically with the cellulose particles to provide a durable covalent bond thereto and have hydrophobic chemical backbones or substituents that can provide a hydrophobic outer layer around each individual cellulose particle. The coating agent may react, for example, with hydroxyl groups, available oxygen atoms present on the surface of the cellulose particle being coated.

Hydrophobic agents may include, but not limited to, low water soluble organic compounds such as metal soap, e.g., a metal myristate, metal stearate, a metal palmitate, a metal laurate or other fatty acid derivatives known to one of skill in the art. Other hydrophobic agents may include an organic wax, such as a synthetic wax like polyethylene or a natural wax like carnauba wax. Hydrophobic agents useful in coating the cellulose particles useful in the compositions and methods of this invention may also be long chain fatty acids or esters such as stearic acid, oleic acid, castor oil, isododecane, silicone, and their derivatives, non-water soluble polymers, e.g. high molecular weight methylcellulose and ethylcellulose, and high molecular water insoluble fluoropolymers etc., polymerized siloxanes or polysiloxanes with the chemical formula [R2SiO]n, where R is an organic group such as methyl, ethyl, or phenyl, such as dimethicone, dimethicone copolyol, dimethicone ester; methicone and their derivatives. Examples of hydrophobic linear cotton particles useful in the present invention include, but are not limited to, Cotton Fiber Flock CD60 available from Goonvean Fiber and W200 White Cotton Flock available from International Fiber Corporation.

The hydrophobic linear cellulose particles of this invention may be formulated into a variety of "leave-on" skin care applications.

The term "leave-on" as used herein indicates that the compositions of this invention are intended to be applied to and allowed to remain on the skin. These leave-on compositions are to be distinguished from compositions which are applied to the skin and subsequently removed either by washing, rinsing, wiping or the like.

The leave-on, hydrophobic linear cellulose particle-containing compositions of this invention may be formulated into a wide variety of leave-on compositions for personal care, including but not limited to lotions, creams, ointments, gels, tonics, sprays, aerosols, conditioners, hand and body lotions, facial moisturizers, solid get sticks, sunscreens, anti-acne preparations, topical analgesics, mascaras, make-ups, anti-perspirants an deodorants.

The topical cosmetic compositions of this invention may contain a carrier, which should be a cosmetically and/or pharmaceutically acceptable carrier. The carrier should be suitable for topical application to the skin, should have good aesthetic properties and should be compatible with other components in the composition.

These product types may comprise several types of cosmetically acceptable topical carriers including, but not limited to solutions, emulsions (e.g., microemulsions and nanoemulsions), gels, solids and liposomes. The following are non-limitative examples of such carriers. Other carriers can be formulated by those of ordinary skill in the art.

The topical compositions useful in accordance to this invention can be formulated as solutions. Solutions typically include an aqueous solvent (e.g., from about 50% to about 99.99% by weight or from about 90% to about 99% by weight of a cosmetically acceptable aqueous solvent).

Topical compositions useful in the subject invention may be formulated as a solution comprising an emollient. Such compositions preferably contain from about 2% to about 50% by weight of an emollient(s). As used herein, "emollients" refer to materials used for the prevention or relief of dryness, as well as for the protection of the skin. A wide variety of suitable emollients is known and may be used herein. Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., $7^{th}$ Edition, 1997) (hereinafter "ICI Handbook") contains numerous examples of suitable materials.

A lotion can be made from such a solution. Lotions typically comprise from about 1% to about 20% by weight (e.g., from about 5% to about 10%) of an emollient(s) and from about 50% to about 90% by weight (e.g., from about 60% to about 80%) of water.

Another type of product that may be formulated from a solution is a cream. A cream typically comprises from about 5% to about 50% by weight (e.g., from about 10% to about 20%) of an emollient(s) and from about 45% to about 85% by weight (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% by weight of an emollient(s) plus from about 0.1% to about 2% by weight of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the ICI Handbook pp. 1693-1697.

The topical compositions useful in this invention can be formulated as emulsions. If the carrier is an emulsion, from about 1% to about 10% by weight (e.g., from about 2% to about 5%) of the carrier comprises an emulsifier(s). Emulsifiers may be nonionic, anionic or cationic. Suitable emulsifiers are disclosed in, for example, U.S. Pat. No. 3,755,560, U.S. Pat. No. 4,421,769, McCutcheon's Detergents and Emulsifiers, North American Edition, pp. 317-324 (1986), and the ICI Handbook, pp. 1673-1686.

Lotions and creams can be formulated as emulsions. Typically such lotions comprise from 0.5% to about 5% by weight of an emulsifier(s). Such creams would typically comprise from about 1% to about 20% by weight (e.g., from about 5% to about 10%) of an emollient(s); from about 20% to about 80% by weight (e.g., from 30% to about 70%) of water; and from about 1% to about 10% by weight (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. Nos. 4,254,105 and 4,960,764, are also useful in the subject invention. In general, such single or multiphase emulsions contain water, emollients, and emulsifiers as essential ingredients.

The topical compositions of this invention can also be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents.

The topical leave-on compositions of this invention may also be formulated as a suspension. In such a case, the compositions of this invention preferably contain a suspending agent. As used herein, the term "suspending agent" means any material known or otherwise effective in providing suspending, gelling, viscosifying, solidifying and/or thickening properties to the composition or which otherwise provide structure to the final product form. These suspending agents include gelling agents, and polymeric or non-polymeric or inorganic thickening or viscosifying agents. Such materials will typically be solids under ambient conditions and include organic solids, silicone solids, crystalline or other gellants, inorganic particulates such as clays or silicas, or combinations thereof.

The concentration and type of suspending agent selected for use in the topical leave-on compositions of this invention will vary depending upon the desired product hardness, rheology, and/or other related product characteristics. For most suspending agents suitable for use herein, total concentrations range from about 0.1% to about 40% by weight, more typically from about 0.1% to about 35%, by weight of the composition. Suspending agent concentrations will tend to be lower for liquid embodiments (e.g., pressurized or other liquid sprays, roll-ons, etc) and higher for semi-solid (e.g., soft solids or creams) or solid stick embodiments.

Non limiting examples of suitable suspending agents include hydrogenated castor oil (e.g., Castor wax MP80, Castor Wax, etc.), fatty alcohols (e.g., stearyl alcohol), solid paraffins, triglycerides and other similar solid suspending esters or other microcrystalline waxes, silicone and modified silicone waxes. Non limiting examples of optional suspending agents suitable for use herein are described in U.S. Pat. No. 5,976,514 (Guskey et al.), U.S. Pat. No. 5,891,424 (Bretzler et al.), which descriptions are incorporated herein by reference.

Other suitable suspending agents include silicone elastomers at concentrations ranging from about 0.1% to about 10%, by weight of the composition. Non-limiting examples of such silicone elastomer materials suitable for use as a suspending agent herein are described in U.S. Pat. No. 5,654,362 (Schulz, Jr. et al.); U.S. Pat. No. 6,060,546 (Powell et al.) and U.S. Pat. No. 5,919,437 (Lee et al.), which descriptions are incorporated herein by reference. These silicone elastomers materials can also be added for their skin feel or other cosmetic benefits alone, or for such benefits in combination with suspending agent benefits.

The topical compositions of this invention can also be formulated into a solid formulation (e.g., a wax-based stick, soap bar composition, powder, or a wipe containing powder).

The topical compositions useful in the subject invention may contain, in addition to the aforementioned components, a wide variety of additional oil-soluble materials and/or water-soluble materials conventionally used in compositions for use on skin, hair, and nails at their art-established levels.

Additional Cosmetically Active Agents

In one embodiment, the topical composition further comprises another cosmetically active agent in addition to the cellulose particles. What is meant by a "cosmetically active agent" is a compound that has a cosmetic or therapeutic effect on the skin, hair, or nails, e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning.

In one embodiment, the agent is selected from, but not limited to, hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, spin traps, retinoids such as retinol and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, peptides such as those disclosed in U.S. Pat. No. 6,620,419, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited to, glycolic acid, lactic acid, malic acid, salicylic acid, citric acid, and tartaric acid and the like.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612-13 of the ICI Handbook.

Other Materials

Various other materials may also be present in the compositions useful in the subject invention. These include humectants, proteins and polypeptides, preservatives and an alkaline agent. Examples of such agents are disclosed in the ICI Handbook, pp. 1650-1667.

The compositions of this invention may also comprise chelating agents (e.g., EDTA) and preservatives (e.g., parabens). Examples of suitable preservatives and chelating agents are listed in pp. 1626 and 1654-55 of the ICI Handbook. In addition, the topical compositions useful herein can contain conventional cosmetic adjuvants, such as dyes, opacifiers (e.g., titanium dioxide), pigments, and fragrances.

It was found that the hydrophobic linear cellulose particles useful in the compositions of this invention have excellent water and oil absorption properties. It is believed that the compositions of this invention contain hydrophobic cellulose particles may absorb excess sebum from the skin, thus reducing skin shininess. The compositions of this invention also are believed to protect the skin barrier by forming a hydrophobic layer on the surface of the skin and preventing the penetration of surfactants, emulsifiers or other potentially irritating ingredients. In addition, such a hydrophobic layer formed on the surface of the skin should reduce trans-epithelial water loss and increase hydration of the skin. However, in some instances, it may be desired that the cellulose particles have enhanced hydrophobic or hydrophilic properties.

Thus, the hydrophobic, linear cellulose particles useful in the compositions of this invention may be treated with additional hydrophobic agents or hydrophilic agents, thus further enhancing hydrophobic and/or hydrophilic properties respectively, as desired. Hydrophobic agents may include but not limited to low water soluble organic compounds such as long chain fatty acids or esters such as stearic acid, oleic acid, castor oil, isododecane, silicone, and their derivatives, non-water soluble polymers, e.g. high molecular weight methylcellulose and ethylcellulose, and high molecular water insoluble fluoropolymers etc., polymerized siloxanes or polysiloxanes with the chemical formula $[R_2SiO]_n$, where R is an organic group such as methyl, ethyl, or pheny, such as dimethicone, dimethicone copolyol, dimethicone ester; methicone and their derivatives. Hydrophilic agents such as water soluble polymers, e.g. low molecular weight methyl cellulose or hydroxypropyl methyl cellulose (PMC); sugars, e.g. monosaccharides such as fructose and glucose, disaccharides such as lactose, sucrose, or polysaccharides such as cellulose, amylose, dextran, etc. and low molecular polyvinyl alcohol, and hydrated silica may also be used to enhance the hydrophilic properties of the cellulose particles used in the compositions of this invention.

It also was found that the textures of the compositions formulated with the hydrophobic linear cellulose particles of this invention are "fluffy", silky and soft and aesthetically pleasing to the touch during and after the application. The term "fluffy" as used herein refers to the bulk density of the hydrophobic linear cellulose particles useful in the compositions of this invention. The bulk density of the hydrophobic linear cellulose particles useful in the compositions of this invention is preferably from about 0.1 to about 2 (g/cm$^3$), more preferably from about 0.15 to about 1.8 g/cm$^3$, and most preferably from about 0.15 to about 1.6 g/cm$^3$. Preferably, the cellulose particles useful in the compositions of this invention are present in the compositions in an amount of from about 1 to about 20% by weight of the compositions, more preferably from about 1 to about 10% by weight of the compositions and most preferably in an amount of from about 1 to about 6% by weight of the compositions.

Methods of Treating or Conditioning the Skin or Hair

The methods of this invention also relate to methods of treating or conditioning the skin or hair with a personal leave-on product of this invention. These methods comprise the steps of applying a substantially dry, disposable, single use personal cleansing product comprising a carrier ingredient and a composition according to this invention and contacting the skin or hair with said product and leaving said product on the skin or hair without removing it. In further embodiments, the methods and compositions of this invention are also useful for delivering various active ingredients to the skin or hair.

The invention will be further described by reference to the following examples in order to further illustrate the present invention and advantages thereof. These examples are not meant to be limiting but illustrative. Compounds are indicated, depending on the case, as their CTFA name or their chemical name, and the percentages are given on a weight basis, except where otherwise mentioned.

EXAMPLES

Example 1

Characterization of Hydrophobic and Hydrophilic Linear Cellulose Fibers

Hydrophobic cotton particles and Hydrophilic Cotton particles listed in Table 1 below were characterized as followed:

Materials:

TABLE 1

| Materials | |
|---|---|
| Squalene | |
| DI Water | |
| Hydrophobic Linear Cotton Particles (available from Goonvean of Cornwall England) | Hydrophobic Particles #1 |
| Hydrophobic Linear Cotton Particles (available from IFC of North Tonawanda, NY) | Hydrophobic Particles #2 |
| Hydrophilic Cotton Particles (available from Resources of Nature of South Plainfield, NJ) | Hydrophilic Particles #1 |

Example 1A

Particle Size Measurement

The particle size of the cellulose materials was determined by Mie/Fraunhofer Laser Scattering method using a Malvern Hydro 2000S Particle Size Analyzer by the following procedure:
1. Ensured the cell windows and lenses are clean and free from scratches.
2. Flushed (using de-ionized water) and drained the accessory at least 2 times in order to eliminate any contamination from previous samples.
3. Turned off the pump/stirrer and turned on the ultrasonics for 30 seconds to allow for air bubbles to dissipate.
4. Filled the dispersion unit with DI water. Adjusted the pump/stirrer speed to 2100 rpm, and then turned off the pump for about 3 seconds to allow the air to dissipate. Then slowly turned the pump back on to 2100 rpm. Toped up the water in the dispersion unit to replace the volume of air displaced.
5. Added 4 drops of 5% IGEPAL CA 630 (non ionic detergent) in the tank and allow dispersing before measuring the background. If this concentration causes bubble formation, cleaned the unit and repeat the procedure using 2 drops of surfactant. To ensure the background give a clean value. Follow the 2-150 and 20-20 rule (First two detectors should have light intensity less than 150 units and the detector number 20 should have light intensity less than 20 units)
6. When the system was clean, added diluted sample to be measured in the dispersion unit in an amount of about 2 mg in 10 grams water.
7. When the obscuration caused by the particles in the sample is 2 to 5%, start the measurement. Note D50 and D90 in microns. (D50 refers to 50% of the particles are less than the value; D90 refers to 50% of the particles are less than the value)
8. The experiment was repeated three times and the average of the three results was recorded as the final value.

The average particle size of various cellulose particles outlined in Table 1 was determined and shown in Table 2.

TABLE 2

| | Particle Size D90 (microns) | Particle Size D80 (microns) | Particle Size D50 (microns) |
|---|---|---|---|
| Hydrophilic Cotton Particles | 170 | 125 | 70 |
| Hydrophobic Linear Cotton Particles Hydrophobic #1 | 500 | 200 | 55 |
| Hydrophobic Linear Cotton Particles Hydrophobic #2 | 270 | 125 | 50 |

Example 1B

Contact Angle

The contact angles of various cellulose particles outlined in Table 1 were determined as follows:

40 Grams of the cotton particles shown in Table 1 were placed in a particle sample holder; the surface was compressed with a consistent force to create a smooth and compact surface of the particles. 500 µl micro syringe filled with test liquid (water), 0.52 mm needle was used to dispense and deposit 5 µl droplets on the surface. Contact Angles of the droplet on each of the cotton particle samples were measured and calculated with Video-based DataPhysics optical contact angle measuring system OCA 20 with software SCA20 from three replicate tests on each sample, results are shown in Table 3.

TABLE 3

| Material | Initial Water Contact Angle (degrees) |
|---|---|
| Hydrophobic Linear Cotton Particles #2 | 136.2 (5.8)* |
| Hydrophilic Cotton Particles | 39.1 (4)* |
| Hydrophobic Linear Cotton Particles #1 | 122.3 (3.2)* |

*represents standard deviation

As shown in Table 3, hydrophobic cotton particles exhibited a larger water contact angle compared to the hydrophilic cotton particles.

Example 1C

Infrared Spectra

Figure 2:
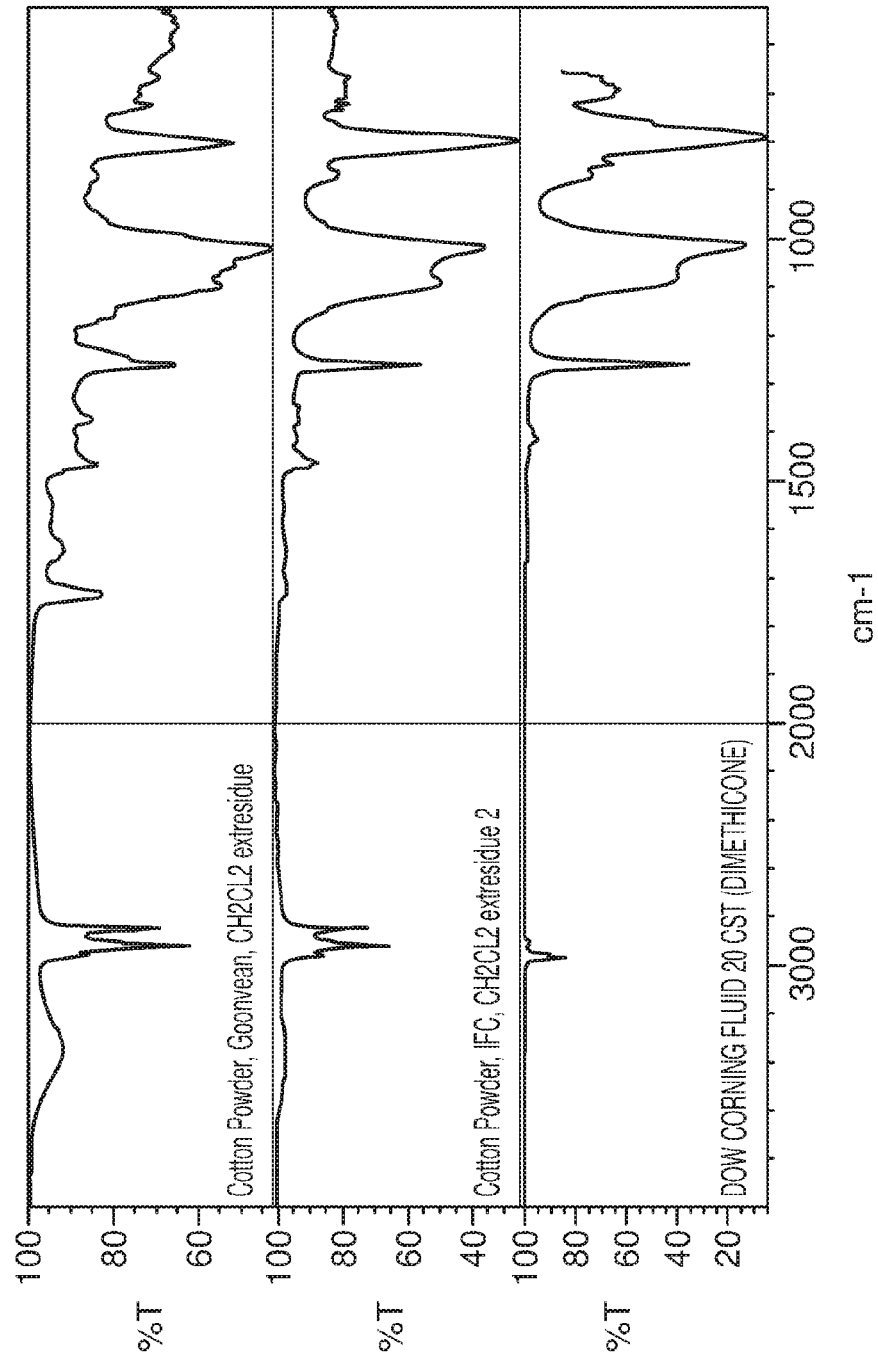
FIG. 2 is a graph of Infrared spectra of various solvent extracts from hydrophobic cotton particles and dimethicone.

Infrared spectrum analysis was performed on three cotton particles as follows:

Solvent extraction of the cotton materials using methylene chloride was conducted and followed by IR analysis of the evaporated residues and forth in FIGS. 1 and 2 hereto.

The spectra (shown in FIGS. 1 and 2) showed extract residues from the two hydrophobic linear cotton particles (#2 and #1) along with a dimethicone reference spectrum.

Solvent extractions of the two hydrophobic cotton materials (IFC and Goonvean) showed a significant amount of waxy semi-solid residue, and relatively little from the hydrophilic cotton materials. It is believed that this waxy semi-solid residue coating is responsible for the hydrophobic nature of these two hydrophobic cotton particles.

Infrared analysis of the #2 and #1 hydrophobic cotton residues shows them both to contain silicone (dimethicone or related polymer) along with other components. The #2 residue includes a long chain hydrocarbon wax-like material (as indicated by split peaks around 1375 and 725 cm-1) while the #1 residue includes an ester component (as indicated by IR peaks around 1735 and 1250 cm-1).

The hydrophilic cotton particles (Virgin Cotton Flock) showed negligible extractable residue. The morphology of this material was significantly different from the other two materials indicating a higher degree of processing, reducing much of the cotton fiber into a fine powdery material. The hydrophilic nature of this material is likely due to the inherent absorbent properties of cotton, and the lack of a repellant finish treatment.

Further, Infrared analysis showed that all three cotton materials are typical "cellulosic" materials. Characterization of the three different cotton materials showed the hydrophobic (#2 and #1) being composed of a silicone based hydrophobic treatment. In contrast, the hydrophilic cotton lacks of the silicone based hydrophobic repellant treatment.

Example 2

Specific Surface Area

Inverse Gas Chromatography (IGC) has been reported in various papers as a good method to determine isotherms at finite concentration and ambient temperatures, using organic probe molecules. (Thielmann, F., Burnett, D. J. and Heng, J. Y. Y. (2007) Determination of the surface energy distributions of different processed lactose. *Drug Dev. Ind. Pharm.* 33, 1240-1253. And see also Yla-Maihaniemi, P. P. et al. (2008) Inverse gas chromatographic method for measuring the dispersive surface energy distribution for particulates. Langmuir, 24, p. 9551-9557.

Specific surface area was determined with IGC using octane by measuring the octane adsorption isotherms at 30° C. and 0% RH. The results of these determinations are shown in Table 4. "BET" is a measurement of specific surface area known to those of ordinary skill in the art.

TABLE 4

Specific surface areas of particles (BET/IGC)

| Sample | Surface area ($m^2$/gr.) |
|---|---|
| Hydrophilic Cotton Particles | 1.4 |
| Hydrophobic Linear Cotton Particles (#1) | 1.23 |
| Hydrophobic Linear Cotton Particles (#2) | 1.6 |

Example 3

Absorption Capacity and Retention

The absorption capacity of olive oil by the dry cotton particles in Table 1 was measured in standard conditions (i.e. ambient temperature and pressure). The saturated particles were also subjected to centrifugal force to measure their retention power.

When porous media containing liquid is subjected to a force, the liquid is gradually evacuated from large pores then from increasingly small pores as pressure increases. Media containing a high pore volume distribution of smaller pores (or effective pores) can retain more liquid under higher constraint and this retentive power may be a useful feature when the desired role of the media is to retain a liquid (sponge effect).

In order to evaluate the retentive power of the particles, over-saturated oil/particles combinations were subjected to centrifugal force (8000 rpm, 300 seconds) and remaining oil was measured. The results of this measurement are shown in Table 5.

After acceleration, the remaining oil can be expressed as a proportion of the amount of the saturating oil (=mass of oil remaining/mass of oil initially in the blend) or else one can express the amount of oil remaining as a mass fraction of the particles/oil mix (=mass of oil remaining/mass of the particles/oil complex). Both calculations may provide different insights and are expressed in the following table.

TABLE 5

Absorption Capacity and Retention of glyceryl trioleate (olive oil) on Cotton Particles.

| Sample | Absorption capacity of olive oil (% w/w) | Retention @ 8000 rpm (% of saturation) | Retention @ 8000 rpm (% of blend) |
|---|---|---|---|
| Hydrophilic Cotton Particles | 130 | 14 | 16 |
| Hydrophobic Linear Cotton Particles (#1) | 445 | 14 | 38 |
| Hydrophobic Linear Cotton Particles (#2) | 322 | 7 | 18 |

The two Hydrophobic Linear Cotton Particles (#1 and #2) demonstrated very high absorption of oil in the dry, loosely packed state. Further, the Hydrophobic Linear Cotton Particles (#1) retained a high amount of triglyceride even under applied acceleration.

Example 4

Speed of Oil Absorption

The speed of oil absorption by a material may be determined by Procedures as follows:

A template of a 6×4 cm rectangle was cut from a 0.25 mm thick paper. With a 4×2 cm rectangle window cut in the middle with 1 cm of paper around the edge of the window. A glass microscope slide was weighed and its mass recorded. The template was placed on the slide and the test material dispensed in the window of the template. The material was spread across the window with a metal spatula to create an even rectangular layer with a mass of ~0.24 g (±0.01 g). The template was carefully removed, edges of the slide cleaned off with a spatula or gloved fingertip as necessary, and the mass of the slide+material recorded. The slide (with oil-absorbing particle layer) was placed flat in an incubator at 32° C. 0.0858 g of the sebum component of interest was dispensed via 0-100 μL pipette (liquids) to the slide at one side of and in contact with the particle layer. (For squalene, 100 μL was used; for triolein, 94.3 μL was used based on suppliers' stated densities). The slide was left undisturbed in the incubator for 15 seconds for follow-up test), with a timer started just as the drop was dispensed. After 15 seconds, the slide was removed from the incubator and any unabsorbed sebum component was carefully wiped from the slide using a Kimwipe. The slide was weighed to determine the amount of the sebum component absorbed by the particles during the absorbance period. The Steps above were repeated for each slide, with each sebum component/particle combination tested at least in triplicate. Ratios were calculated to show the mass of sebum component absorbed per mass of oil-absorbing particles within 15 seconds. The results of this determination are set forth in FIG. 3 hereto.

Figure 3:
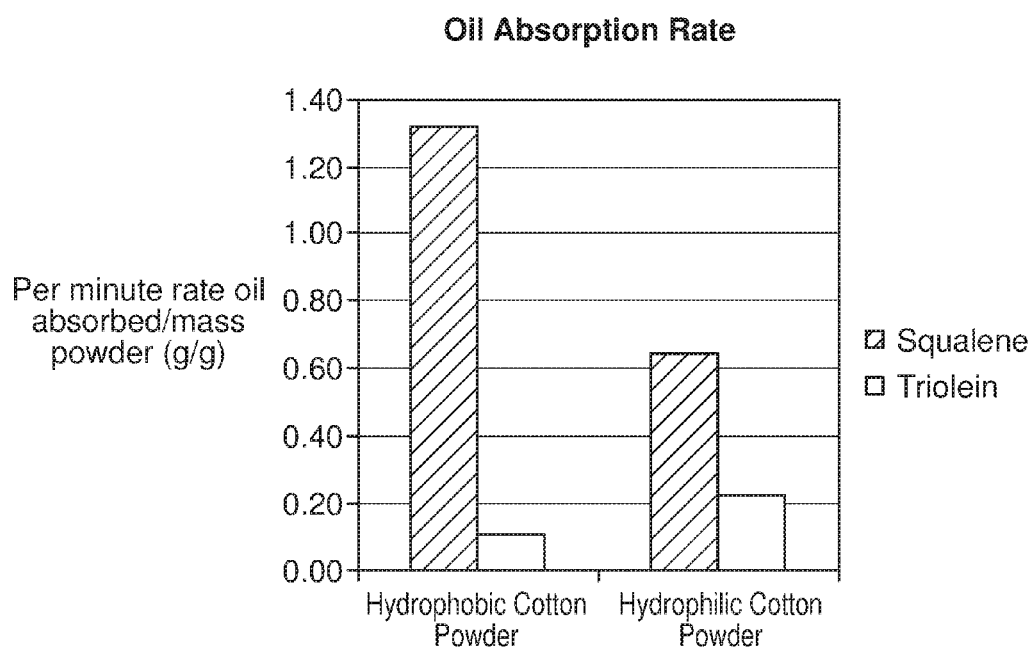
FIG. 3 is a graph illustrating oil absorption rates of hydrophilic and hydrophobic cotton particles.

FIG. 3 demonstrates that hydrophobic cotton particles (#1 hydrophobic cotton particles) absorbs both squalene and triglyceride much faster than hydrophilic cotton particles.

Example 5

Speed of Water Absorption

The speed of water absorption of materials was determined by the procedure set forth as follows:

A gravimetric absorption test (GAT) Method was used to determine the water absorption kinetics of hydrophobic cotton particles vs. hydrophilic cotton particles. The cotton particles sample was loaded into a small cylinder container, and the water was introduced in contact with the cotton particles through a water reservoir on a scale, the change in water weight arising from water transfer or absorption by cotton particles was recorded electronically by a computer over the study duration. The absorption rate was calculated and plotted for different cotton particles samples.

Figure 4:
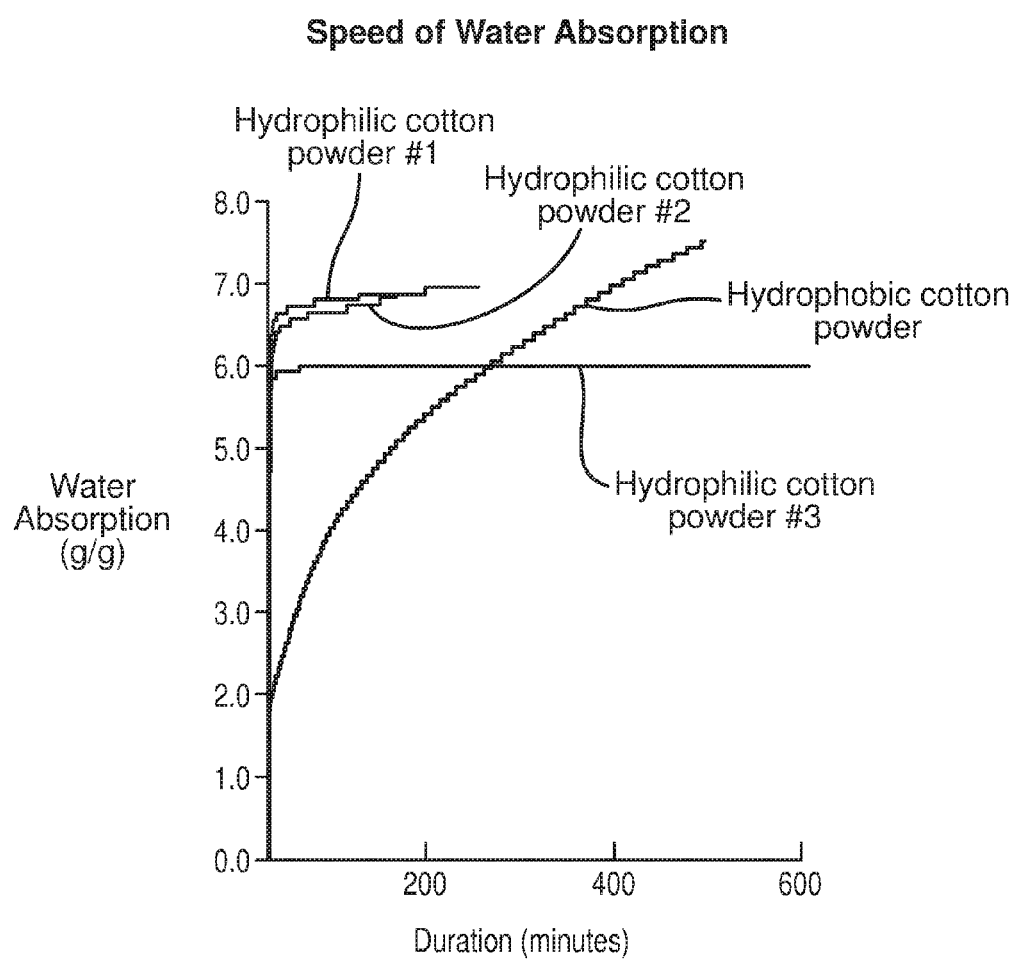
FIG. 4 is a graph of the speed of water absorption measured from various hydrophobic and hydrophilic cotton particles.

As shown in FIG. 4, hydrophobic cotton particles had a slower water absorption rate than hydrophilic cotton particles.

Example 6

Water Absorption Capacity and Oil Absorption Capacity

The water absorption capacity and oil absorption capacity of materials may be determined by the following procedures set forth below in Examples 6A and 6B.

Each experiment was repeated in triplicate for #1 hydrophobic Cotton particles, hydrophilic Cotton particles (#1), and #2 hydrophobic Cotton particles.

Example 6A

Measurement of Hydrophobicity and Oil Absorption

Figure 5:
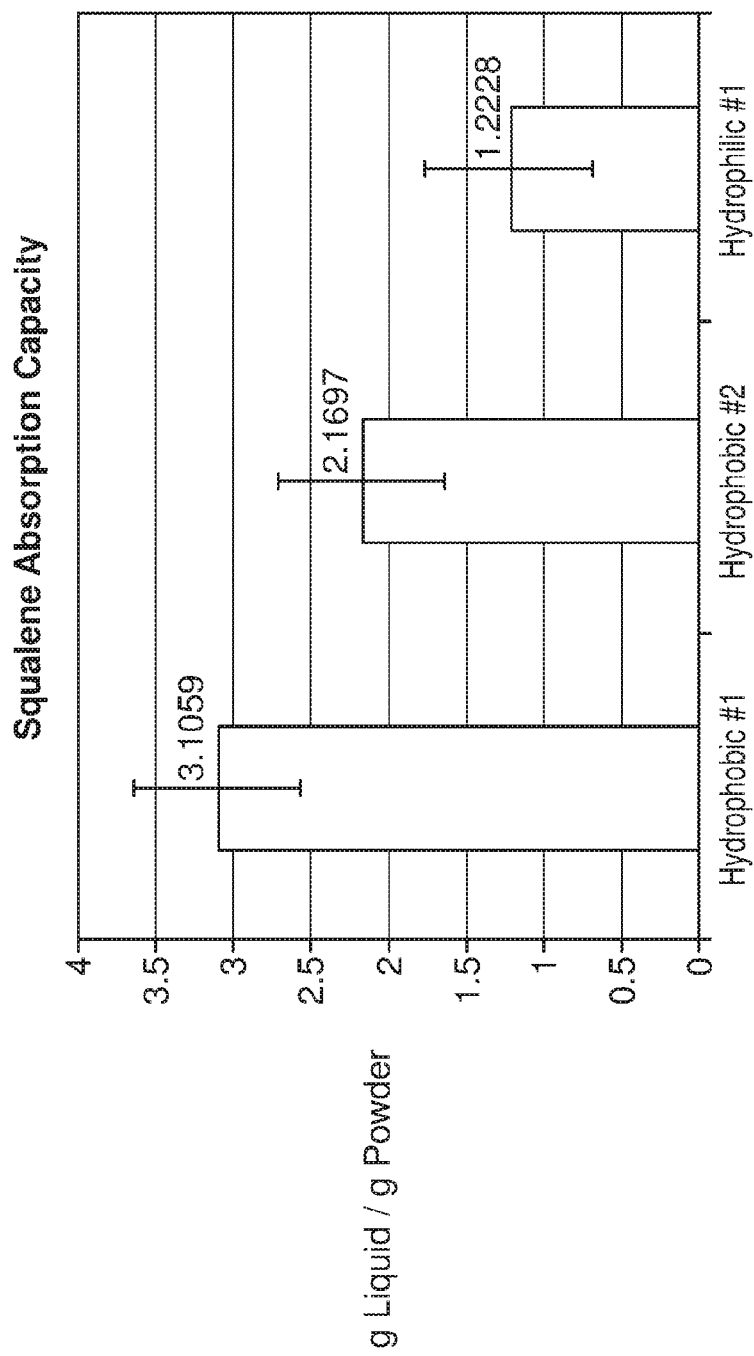
FIG. 5 is a graph illustrating average oil absorption capacity of various hydrophobic and hydrophilic cotton particles.

The scale was tared with the particles samples. Squalene was then added drop by drop via disposable pipette until the sample looked nearly saturated. A metal spatula was used to completely mix in the oil with the particles until saturated (After mixing, the spatula was wiped clean against the side of the weigh boat to ensure there was no loss of material). "Saturation" as used herein is defined as the mixture being able to hold all the available squalene such that the bottom of the boat appeared dry. This determination was based on the appearance of the mixture and the condition of the weigh boat. The total number of grams of squalene was recorded and the relative Oil Absorption ratio was calculated by dividing the total weight of oil by the total weight of cotton materials. The results of performing this procedure are set forth in FIG. 5 hereto.

Example 6B

Measure Water Absorption

Figure 6:
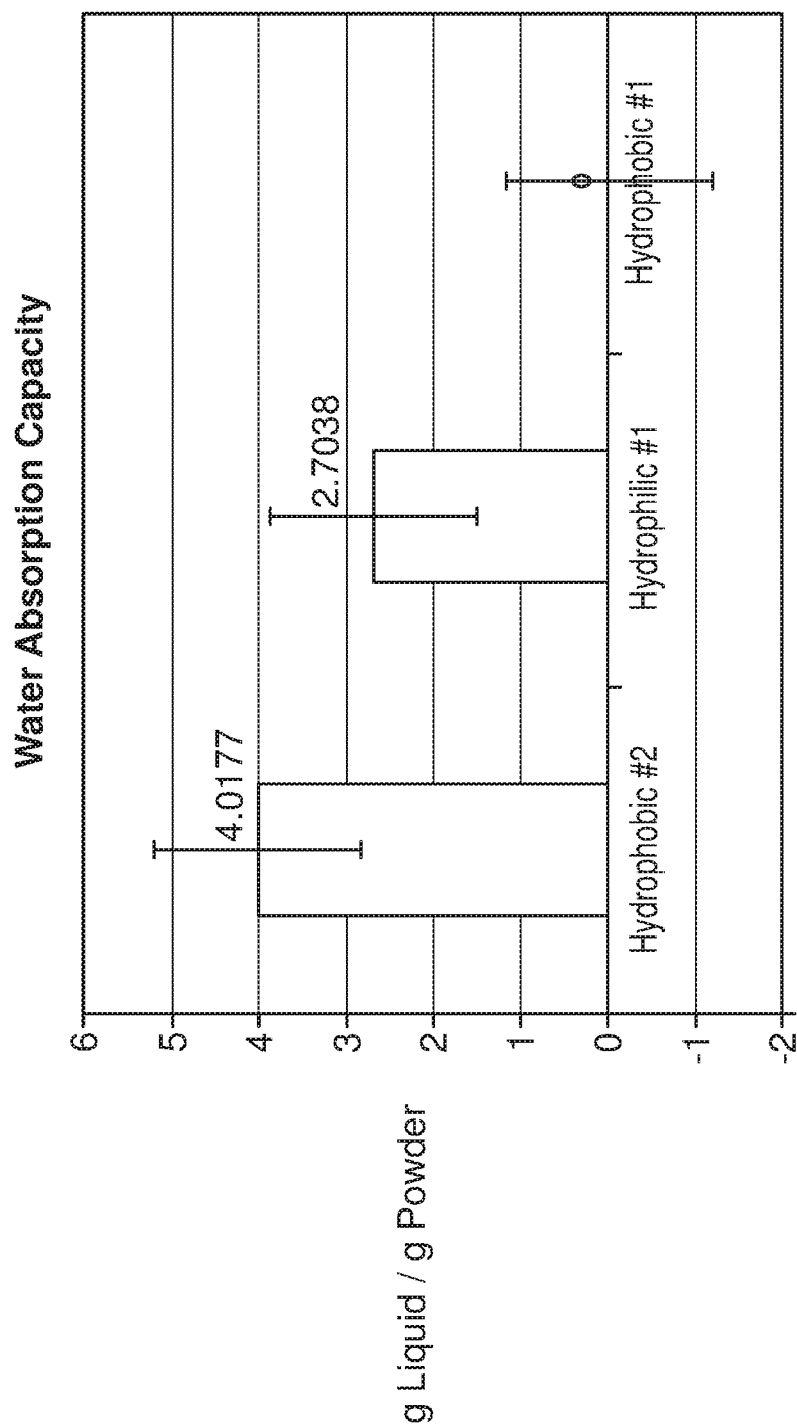
FIG. 6 is a graph illustrating average water absorption capacity of various hydrophobic and hydrophilic cotton particles.

Following a method similar to that described in example 6A, but substituting water for the oil material, water absorption was measured. The results of this test are set forth in FIG. 6.

Example 7

Retention of Oil

The Retention of Oil was determined by the following procedure:

A test site was marked with a circle with 2 cm diameter on an oil impermeable white card. About 6.2 mg of artificial sebum was applied uniformly inside the marked circle to create an oily patch with a Sebumeter reading recorded as pretreatment sebum reading P. Weighed about 25 mg of the test sample and apply it uniformly onto the test site. Measured the sebum within each test with a sebumeter to site and recorded the sebumeter readings 10 minutes after product application. The procedure was repeated for 2 replicas for each test product and the average S was calculated to give the sebum level with product application.

The in-vitro sebum absorption is calculated using the following equation:

$$\% \text{ Sebum level change}=(S-P)/P$$

Where S=Average Pre-treatment Sebumeter Reading
P=Average Post-treatment Sebum Reading The oil absorption in-vitro studies were conducted at the initial and three months' room temperature (RT) storage (22° C.) for the leave-in conditioners listed in the table below. The in-vitro sebum absorption testing showed that the addition of hydrophobic cotton particles (#1) at 2% level in a leave-in conditioner Formulation B increased the sebum absorption in-vitro by 2× times vs. the leave-in conditioner Placebo Formulation A. Formula B of 2% hydrophobic cotton particles (#1) leave-in conditioner has a slightly higher but not significantly different sebum absorption in-vitro than Formulation C of 2% hydrophilic cotton particles leave-in conditioner.

TABLE 6

| Ingredient (%) | Formula A % | Formula B % | Formula C % |
| --- | --- | --- | --- |
| Deionized Water | 87.81 | 85.81 | 85.81 |
| Hydroxyethylcellulose | 0.50 | 0.50 | 0.50 |
| Part #1 | | | |
| Quaternium 91 and Cetrimonium Methosulfate and Cetearyl Alcohol | 1.00 | 1.00 | 1.00 |
| Behenyl Alcohol | 1.50 | 1.50 | 1.50 |
| Stearyl Alcohol | 1.25 | 1.25 | 1.25 |
| Cetyl Alcohol | 3.00 | 3.00 | 3.00 |
| Part #2 | | | |
| Dimethicone | 1.00 | 1.00 | 1.00 |
| Amodimethicone | 0.25 | 0.25 | 0.25 |
| Dimethicone | 2.00 | 2.00 | 2.00 |
| Part #3 | | | |
| Polyquaternium-37 and Propylene Glycol Dicaprate/Dicaprate and PPG-1 Trideceth-6 | 0.20 | 0.20 | 0.20 |
| Phenoxyethanol & Caprylyl Glycol | 1.00 | 1.00 | 1.00 |
| Water (and) Hydrolyzed Lupine Seed Extract | 0.01 | 0.01 | 0.01 |
| Fragrance | 0.35 | 0.35 | 0.35 |
| hydrophobic Cotton particles (#1) | | 2.00 | |
| Hydrophilic Cotton particles | | | 2.00 |
| Sodium Hydroxide | 0.13 | 0.13 | 0.13 |
| Total | 100.00 | 100.00 | 100.00 |

The compositions set forth in Table 6 were prepared in accordance with the following method:

1. Deionized water and hydroxyethylcellulose were added into a mixing container and heated to 75°-80° C.
2. In a separate container, the ingredients set forth in Table 6 above as Part #1 were added and heated to 75°-80° C. until all the ingredients are melted. 3. After all of Part #1 ingredients WERE melted, the hydroxyethylcellulose solution was phased with Part #1 and mixed until homogeneous. Cooling to below 40° C. was then begun.
4. At 60°-65° C. the Part #2 ingredients were added one at a time allowing for good mixing and mixed until the batch was homogeneous.
5. At or below 40° C. the Part #3 ingredients were added.
6. In a separate container, sodium hydroxide and DI water were premixed and the pH of the batch adjusted to pH 4.0-4.5.
7. The ingredients were adjusted to 100% weight per weight in the batch and the batch was homogenized for 1-5 minutes.
8. The cotton particles were added and the batch mixed until it was homogeneous.

Figure 7:
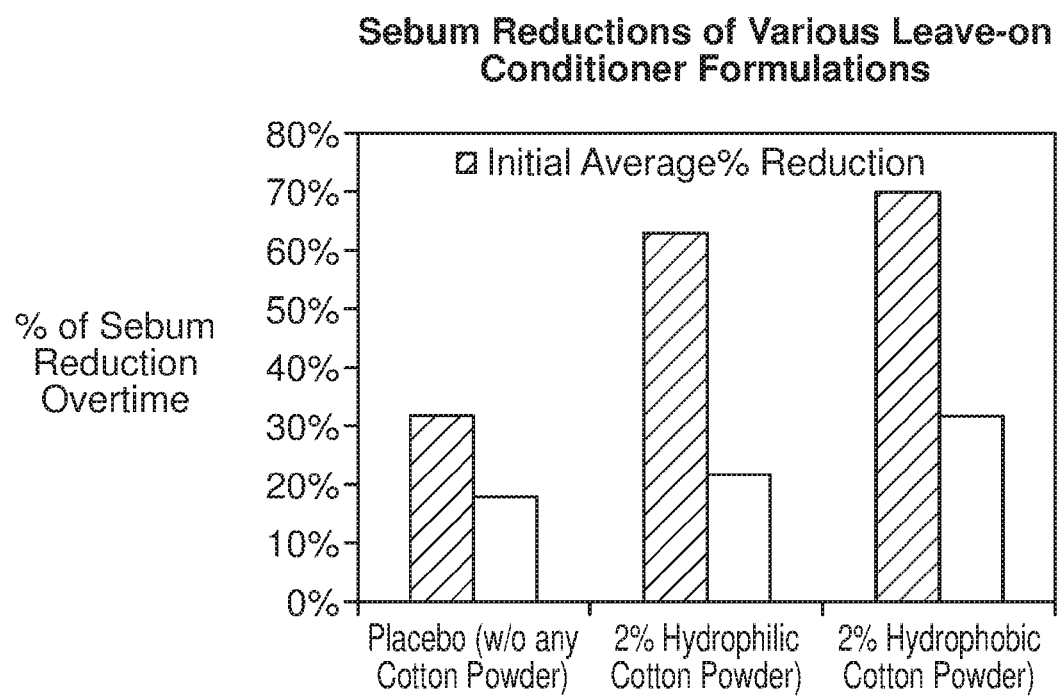
FIG. 7 is a graph illustrating the sebum reduction of skin exposed to various leave-in conditioner compositions of this invention.

The degree of sebum absorption resulting from the above-mentioned procedure for each composition (Formulations A through C) is reflected in the graph set forth in FIG. 7 hereto. As shown therein, hydrophobic cotton powder retained a significantly higher amount of oil (i.e., sebum) for leave-in hair conditioning compositions than compositions containing Hydrophilic cotton particles.

Example 8

Sunscreen Composition

Leave-on sunscreen compositions according to this invention may be made in accordance with the previous examples using the following ingredients:

| Ingredient List | #1 Use range % wt/wt | #2 Use range % wt/wt | #3 Use range % wt/wt |
| --- | --- | --- | --- |
| Purified water | qs | q.s | qs. |
| Lauryl PEG/PPG-18/18 Dimethicone | — | — | 0.00-2.00 |
| Carbomer | 0.00-1.00 | — | — |
| Acrlates/C10-30 Alkyl Acrylate Cross Polymer | — | 0.00-1.00 | — |
| Dimethicone | — | — | 0.000-15.00 |
| Glycerin | 0.00-10.00 | 0.00-10.00 | 0.00-10.00 |
| Disodium EDTA | 0.00-1.00 | 0.00-1.00 | 0.00-1.00 |
| Potassium Cetyl Phosphate | 0.00-5.00 | 0.00-5.00 | — |
| Triethanolamine | 0.00-1.00 | 0.00-1.00 | — |
| BHT | 0.00-1.00 | 0.00-1.00 | 0.00-1.00 |
| Steareth-21 | 0.00-2.00 | 0.00-2.00 | — |
| Steareth-2 | 0.00-1.00 | 0.00-1.00 | — |
| Isododecane | — | — | 0.00-30.00 |
| Cetyl alcohol | 0.00-5.00 | 0.00-5.00 | — |
| Ethylhexyl Methoxycinnamate | — | — | 0.00-10.00 |
| Phenylbenzimidazole Sulfonic acid | — | — | 0.00-5.00 |
| Zinc oxide | 0.00-10.00 | 0.00-10.00 | 0.00-10.00 |
| Titanium Dioxide | 0.00-12.00 | 0.00-12.00 | 0.00-12.00 |
| C12-15 Alkyl Benzoate | 0.00-10.00 | 0.00-10.00 | 0.00-10.00 |
| Preservatives | 0.00-2.00 | 0.00-2.00 | 0.00-2.00 |
| Hydrophobic Cotton particles | 0.00-5.00 | 0.00-5.00 | 0.00-5.00 |
| Fragrance | q.s. | q.s. | q.s. |
| Sodium hydroxide | q.s | q.s | q.s. |
| Total | 100 | 100 | 100 |

Example 9

Liquid Make Up with Cotton Particles

Leave-on liquid make-up compositions according to this invention may be made in accordance with the previous examples using the following ingredients:

| INCI Name | % wt/wt | % wt/wt | % wt/wt |
|---|---|---|---|
| Sodium chloride | 1.00 | 1.00 | 1.00 |
| Butylene Glycol | 2.00 | 2.00 | 2.00 |
| Disodium EDTA | 0.20 | 0.20 | 0.20 |
| Dimethicone | 9.90 | 9.90 | 9.90 |
| C30-45 alkyl methicone and olefin | 1.20 | 1.20 | 1.20 |
| Isododecane | 12.20 | 12.20 | 12.20 |
| Phenoxyethanol | 1.00 | 1.00 | 1.00 |
| Cetyl PEG/PPG-10/1 Dimethicone | 4.00 | 4.00 | 4.00 |
| VP/Hexadecene Copolymer | 1.00 | 1.00 | 1.00 |
| Dimethicone/PEG 10/15 crosspolymer-dimethicone | 6.00 | 6.00 | 6.00 |
| Dimethicone | 3.60 | 3.60 | 3.60 |
| Titanium Dioxide (and) Triethoxycaprylylsilane | 8.00 | 8.00 | 8.00 |
| Iron Oxide (and) Triethoxycaprylylsilane | 1.68 | 1.68 | 1.68 |
| Iron Oxide (and) Triethoxycaprylylsilane | 0.44 | 0.44 | 0.44 |
| Iron Oxide (and) Triethoxycaprylylsilane | 0.26 | 0.26 | 0.26 |
| Salicylic acid | | 0.50-2.00 | |
| Sulfur | | | 3.00-10.00 |
| Hydrophobic Cotton particles | 0-20 | 0-20 | 0-20 |
| DI Water | q.s. | q.s | q.s |
| citric acid 10% solution, adjust to PH = 4-5 | | | |
| Total | 100 | 100 | 100 |

What is claimed is:

1. A leave-on skin care composition comprising: a non-ionic emulsifier in an amount of from 0.5% to 5% by weight of the composition; linear cotton particles in an amount of about 1% to about 20% by weight of the composition, the linear cotton particles having an aspect ratio of from about 2 to about 20 and having a water contact angle of greater than 90 degrees, wherein the cotton particles are generated from cloth or nonwoven materials; a suspending agent present in an amount of from 0.1 to 35% by weight of the composition; at least one sunscreen agent; and a cosmetically acceptable carrier.

2. The leave-on skin care composition according to claim 1 wherein said composition further comprises an aqueous solvent.

3. The leave-on skin care composition according to claim 1 wherein said composition further comprises at least one emollient.

4. The leave on skin care composition according to claim 1, wherein said linear cotton particles have a length of from about 10 microns to about 500 microns.

5. The leave-on skin care composition according to claim 1 wherein said linear cotton particles are present in an amount of from about 1 to about 10 percent by weight of the composition.

6. The leave-on skin care composition according to claim 1 wherein said linear cotton particles are present in an amount of from about 1 to about 6 percent by weight of the composition.

7. The leave-on skin care composition according to claim 1 wherein the non-ionic emulsifier is present in an amount of from about 0.5% to about 2% by weight of the composition.

8. The leave-on skin care composition according to claim 1 wherein the non-ionic emulsifier is present in an amount of from about 0.5% to about 1% by weight of the composition.

9. The leave-on skin care composition according to claim 1 wherein the non-ionic emulsifier comprises potassium cetyl phosphate.

10. The leave-on skin care composition according to claim 1 wherein the suspending agent is selected from the group consisting of hydrogenated castor oil, fatty alcohols, solid paraffins, triglycerides and solid suspending esters or other microcrystalline waxes, silicone, modified silicone waxes, and silicone elastomers.

11. The leave-on skin care composition according to claim 1, wherein the at least one sunscreen agent comprises zinc oxide.

12. The leave-on skin care composition according to claim 9, wherein the at least one sunscreen agent comprises zinc oxide.

* * * * *